United States Patent
Ormando et al.

(10) Patent No.: US 10,480,440 B2
(45) Date of Patent: Nov. 19, 2019

(54) PARTICULATE MATTER SENSOR HEAT COVER

(71) Applicant: GM GLOBAL TECHNOLOGY OPERATIONS LLC, Detroit, MI (US)

(72) Inventors: Alessandro Ormando, Turin (IT); Francesco Cannarile, Turin (IT)

(73) Assignee: GM GLOBAL TECHNOLOGY OPERATIONS LLC, Detroit, MI (US)

(*) Notice: Subject to any disclaimer, the term of this patent is extended or adjusted under 35 U.S.C. 154(b) by 101 days.

(21) Appl. No.: 15/810,185

(22) Filed: Nov. 13, 2017

(65) Prior Publication Data

US 2019/0145332 A1   May 16, 2019

(51) Int. Cl.
| | |
|---|---|
| *F02D 41/14* | (2006.01) |
| *G01N 15/06* | (2006.01) |
| *G01N 7/10* | (2006.01) |
| *F01N 13/00* | (2010.01) |

(52) U.S. Cl.
CPC .......... *F02D 41/1445* (2013.01); *G01N 7/10* (2013.01); *G01N 15/0656* (2013.01); *F01N 13/008* (2013.01); *F01N 2510/00* (2013.01); *F01N 2560/05* (2013.01)

(58) Field of Classification Search
CPC ................................................. F02D 41/1445
USPC ....................................................... 73/28.02
See application file for complete search history.

(56) References Cited

U.S. PATENT DOCUMENTS

| | | | | |
|---|---|---|---|---|
| 5,765,332 A | * | 6/1998 | Landin ................... | E04B 1/948 52/235 |
| 6,971,258 B2 | | 12/2005 | Rhodes et al. | |
| 2013/0037105 A1 | * | 2/2013 | Aitken .................... | C03C 3/087 136/258 |
| 2015/0000389 A1 | * | 1/2015 | Runde .................... | F01N 13/008 73/114.75 |
| 2015/0329408 A1 | * | 11/2015 | Bookbinder ............ | C03C 3/045 428/410 |
| 2017/0234786 A1 | * | 8/2017 | Weber .................. | G01M 15/102 73/23.33 |
| 2018/0149070 A1 | * | 5/2018 | Kawakami .............. | F01N 13/10 |

FOREIGN PATENT DOCUMENTS

CN       1951687 B   *   11/2011

OTHER PUBLICATIONS

English translation of CN1951687 specification from espacenet. Accessed Apr. 17, 2019.*

* cited by examiner

*Primary Examiner* — Nimeshkumar D Patel
*Assistant Examiner* — Jean F Morello
(74) *Attorney, Agent, or Firm* — Harness, Dickey & Pierce, P.L.C.

(57) ABSTRACT

A heat cover for a particulate matter sensor includes an aluminum foil external layer and an internal layer made from a composition including $SiO_2$ of between 52-60%, CaO of between 16-25%, and $Al_2O_2$ of between 12-16%. The heat cover is formed as a sleeve structure and includes an open end for receiving the particulate matter sensor.

2 Claims, 2 Drawing Sheets

PARTICULATE MATTER SENSOR HEAT COVER

FIELD

The present disclosure relates to a heat cover for a particulate matter sensor.

BACKGROUND

This section provides background information related to the present disclosure which is not necessarily prior art.

An exhaust particulate matter sensor monitors the efficiency of a diesel particulate filter (DPF). Due to vehicle manufacturing constraints, a sensor control module of the particular matter sensor is installed very close to the engine exhaust line and often in the engine compartment where the ambient temperature can reach up to 150° C. during certain vehicle operation conditions. Although the sensors are resistant to high temperatures, there is a need to thermally protect the sensor in order to avoid overheating damage under extremely high temperatures.

SUMMARY

This section provides a general summary of the disclosure, and is not a comprehensive disclosure of its full scope or all of its features.

A heat cover for a particulate matter sensor includes an aluminum foil external layer and an internal layer made from a composition including $SiO_2$ of between 52-60%, CaO of between 16-25%, and $Al_2O_2$ of between 12-16%. The heat cover is formed as a sleeve structure and includes an open end for receiving the particulate matter sensor.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
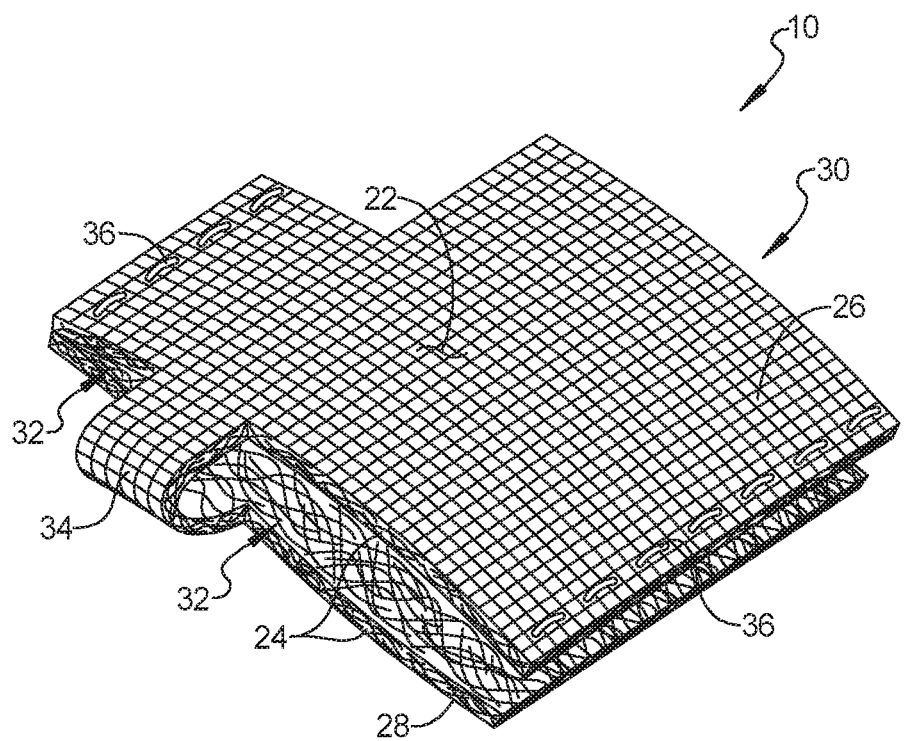
FIG. 1 is a perspective view of a heat cover for a particulate matter sensor according to the principles of the present disclosure.
Figure 2:
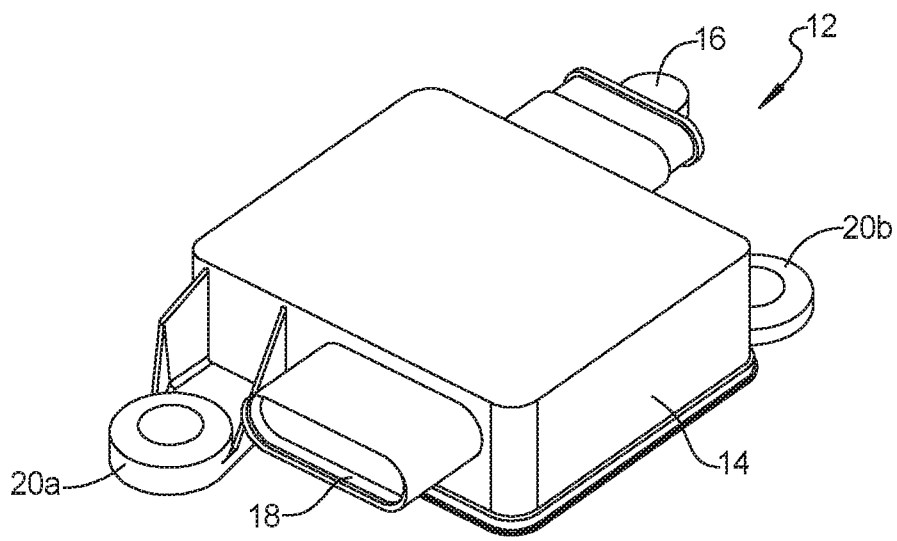
FIG. 2 is a perspective view of an exemplary particulate matter sensor.
Figure 3:
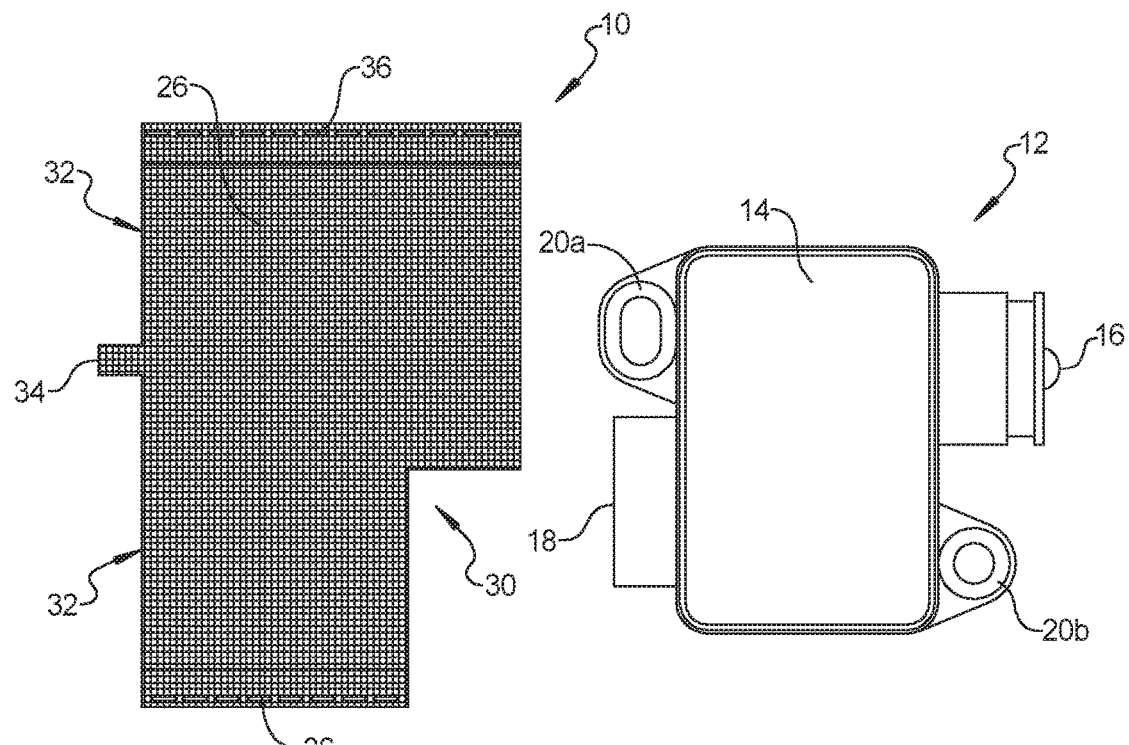
FIG. 3 is a top plan view of a heat cover and particulate matter sensor in a disassembled condition.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIGS. 1-4, a heat cover 10 for a particulate matter sensor 12 according to the principles of the present disclosure will now be described. The exemplary particulate matter sensor 12 generally includes a housing 14, a probe 16 and an electrical interface 18. The housing 14 includes mounting features 20a, 20b extending therefrom for mounting to the vehicle. A sensor control module is disposed within the housing 14 and is in communication with the probe 16 and the electrical interface 18 for providing signals to a vehicle control unit representative of the particulate matter build-up level.

Figure 4:
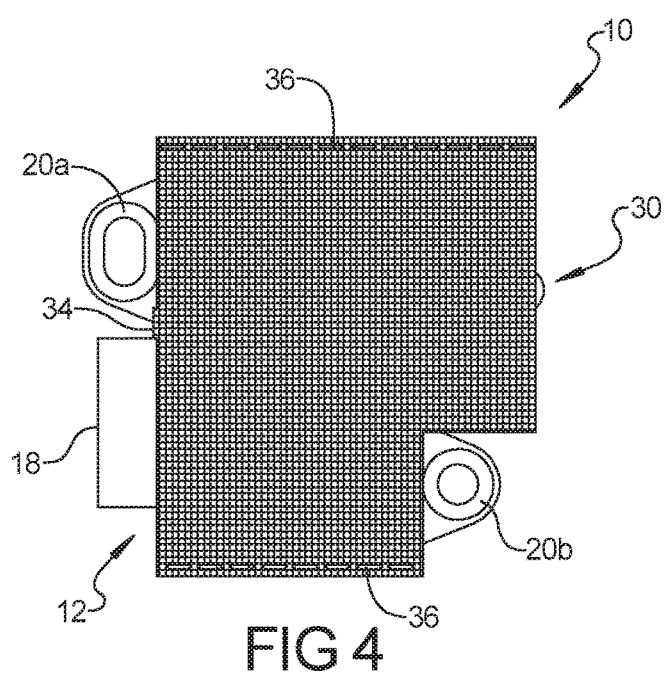
FIG. 4 is a top plan view of the heat cover assembled over top of the particular matter sensor according to the principles of the present disclosure.

The heat cover 10 includes an external layer 22 made of pure aluminum foil and an internal layer 24 made from fiber glass "E" type with a composition including $SiO_2$ of between 52-60%, CaO of between 16-25%, $Al_2O_2$ of between 12-16% and between 8-20% of other oxides. The heat cover 10 can be formed as a sleeve structure having an upper portion 26 and a lower portion 28 to receive the particulate matter sensor 12. The heat cover 10 can include an open end 30 for receiving the housing 14 of the particulate matter sensor 12 between the upper portion 26 and the lower portion 28. Additional openings 32 can be provided through which the electrical interface 18 and the mounting feature 20a can extend, as shown in FIG. 4. The upper and lower portions 26, 28 can be cut into a desired shape with a connecting strap portion 34 and sewn together along seam edges 36. As shown in the assembled condition in FIG. 4, the particulate matter sensor 12 can be inserted into the open end 30 of the heat cover 10. In the assembled condition, electrical interface 18 and the mounting feature 20a can extend through the additional openings 32 with the connecting strap 34 disposed between the electrical interface 18 and the mounting feature 20a.

The aluminum external layer 22 of the heat cover 10 is highly reflective in order to deflect heat away from the particulate matter sensor 12. The internal layer 24 of the heat cover is nonflammable and insulates the particulate matter sensor 12 from heat. The heat cover 10 protects the particulate matter sensor 12 from high heat at a low cost. The heat cover 10 has a compact design and provides improved insulating qualities for all vehicle applications.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A heat cover and particulate matter sensor assembly, comprising:

the particulate matter sensor including a housing with a probe extending therefrom and an electrical interface; and the heat cover formed as a sleeve structure and including an open end receiving the housing of the particulate matter sensor within the sleeve structure, wherein the heat cover includes an aluminum foil external layer and an internal layer made from a composition including $SiO_2$ of between 52-60%, CaO of between 16-25%, and $Al_2O_2$ of between 12-16%, wherein the sleeve structure includes a first layer and a second layer that are sewn together along the side edges thereof and the sleeve structure includes a connecting strap extending between the first and second layers.

2. The heat cover and particulate matter sensor assembly according to claim 1, wherein the internal layer further includes between 8-20% of oxides other than $SiO_2$, CaO and $Al_2O_2$.

* * * * *